(12) United States Patent
Simonov et al.

(10) Patent No.: US 8,979,270 B2
(45) Date of Patent: Mar. 17, 2015

(54) CORNEAL TOPOGRAPHER

(75) Inventors: Aleksey Nikolaevich Simonov, Den Haag (NL); Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 65 days.

(21) Appl. No.: 13/695,842

(22) PCT Filed: May 2, 2011

(86) PCT No.: PCT/NL2011/050297
§ 371 (c)(1),
(2), (4) Date: Jan. 14, 2013

(87) PCT Pub. No.: WO2011/139148
PCT Pub. Date: Nov. 10, 2011

(65) Prior Publication Data
US 2013/0201451 A1    Aug. 8, 2013

(30) Foreign Application Priority Data
May 4, 2010   (NL) ...................................... 2004659

(51) Int. Cl.
*A61B 3/107*    (2006.01)
(52) U.S. Cl.
CPC ..................................... *A61B 3/107* (2013.01)
USPC ........... 351/212; 351/200; 351/205; 351/206; 351/211
(58) Field of Classification Search
CPC ...... A61B 3/0008; A61B 3/10; A61B 3/1005; A61B 3/101; A61B 3/1015; A61B 3/107; A61B 3/14
USPC ......................................... 351/200, 211, 212
See application file for complete search history.

(56) References Cited

U.S. PATENT DOCUMENTS

| | | | |
|---|---|---|---|
| 2004/0021874 A1* | 2/2004 | Shimmick | ...................... 356/497 |
| 2006/0206102 A1* | 9/2006 | Shimmick | .......................... 606/4 |
| 2008/0285043 A1* | 11/2008 | Fercher et al. | ................. 356/451 |
| 2011/0202044 A1* | 8/2011 | Goldshleger et al. | ............. 606/4 |

FOREIGN PATENT DOCUMENTS

WO         9829708 A1      7/1998

OTHER PUBLICATIONS

Nayar, et al., Real-Time Focus Range Sensor, IEEE, Proc. Int',1 Conf. on Computer Vision, Jun. 1995, 995-1,001.

* cited by examiner

*Primary Examiner* — Suchin Parihar
*Assistant Examiner* — William R Alexander
(74) *Attorney, Agent, or Firm* — The Webb Law Firm

(57) ABSTRACT

This invention describes a corneal topographer with a light source to project a pattern light on the cornea, imaging optics for collecting the reflection from the cornea and projecting it on to a photo-sensor, an optical mask to modulate the light beam such that focusing error of the corneal image results in displacement of its spatial spectrum relative to a reference spectrum. Defocus maps, depth-maps and a corneal topogram can be constructed by measuring and processing the spectral displacement corresponding different sub-regions of the cornea. The cornea topographer is compact and inexpensive. The corneal topograph can be used in refractive eye surgery and in contact lens fitting.

6 Claims, 2 Drawing Sheets

CORNEAL TOPOGRAPHER

BACKGROUND OF THE INVENTION

1. Field of the Invention

Corneal topography is a diagnostic technique to measure, generally, the shape of the anterior surface of the cornea. Such measurements are important for determining the refractive optical characteristics of the human eye in refractive surgery and for the design of intraocular lenses (IOLs). A corneal topogram, providing the corneal shape, is required also for fitting of contact lenses. A concept for a novel corneal topographer is described in the present document.

2. Description of the Related Art

Current cornea topographers generally project a set of concentric rings on the anterior cornea and analyze the reflections, i.e. the Placido disc, for changes in shape versus a reference image. The irregularities of the corneal shape can be recalculated from the geometrical distortions of the reflected image. Other corneal topographers use wave-front sensing (e.g., the Shack-Hartmann method) for corneal surface characterization. The present invention is based on measuring absolute distances to the sub-regions of the cornea by analyzing the spatial spectrum of the reflected light.

SUMMARY OF THE INVENTION

The corneal topographer described in the present document is preferably a compact device, without moving parts, comprising standard imaging optics in combination with, at least one, chiral optical mask, a photo-sensor, digital processing means and, optionally, display means. The cornea topographer provides defocus-maps and depth-maps of the corneal surfaces by analyzing the spatial spectrum of Purkinje reflections from the corneal surfaces, which reflections result from the projection of a regular or irregular light pattern on the eye. The topographer and the processing methods are novel.

EXPLANATION OF TERMS

Chiral optical mask: An optical element producing chiral, or helical, modulation of the phase of a transmitting or of a reflecting light beam. Defocus map: A map depicting variations in defocus versus, in the context of the present invention, the location of a selected sub-region on the corneal surface. A defocus map can either be the final output of the topographer or, alternatively, be the intermediate for construction of a depth-map. Depth map: A map providing the absolute depth, or distance, for selected sub-regions of the cornea. In focus image plane: A plane optically conjugate to an object plane having no focusing error.

Pattern light: Light with multiple contrast features projected on the cornea by a light source, for example, a regular grid of spots, or grid of lines, or an irregular speckle pattern originating from a laser beam scattered by a diffuser. Pattern of lines: A periodic pattern in the spectral domain resulting from a chiral optical mask with a half-aperture prismatic optical component. This pattern can be represented by the modulus of the Optical Transfer Function (OTF) and can be calculated from the amplitude and phase functions of the mask. Object plane/image plane: The object, in the context of this invention, a cornea surface illuminated by the pattern light, is positioned in the object plane and the corresponding image is positioned in the image plane. The terms object and image refer to distributions of light in the object and image planes, respectively. Corneal image: An image on the photo-sensor, i.e. in the image plane, resulting from the light reflected by the corneal surface, transmitted by the imaging optics, and modulated by the chiral optical mask. Spectral response/spectral decomposition: The spectral response is generally obtained by Fourier transformation, or another appropriate transformation, or, more generally, by spectral decomposition into a complete set of functions. In practice the spectral response is represented by the incoherent OTF calculated using the mask amplitude and phase functions.

GENERAL DESCRIPTION

The present invention describes a corneal topographer apparatus and methods for corneal shape measurements. The topographer provides: (1)—The degree of defocus of the corneal image, i.e. the image of the corneal surface illuminated by the pattern light on the photo-sensor, relative to the in-focus plane without prior knowledge of the distance to the cornea; (2)—The distance from the cornea to a well-defined plane, preferably the first principal plane of the imaging optics; (3)—The degrees of defocus of multiple sub-regions on the corneal-image relative to the in-focus plane, which sub-regions correspond to the sub-regions on the corneal surface illuminated by the pattern light; (4)—The distance from multiple sub-regions of the cornea to the corneal topographer; (5)—Construction of a depth map representing the corneal surface as a sampled three-dimensional surface, for which the spatial sampling is defined by the structure of the pattern light illuminating the cornea.

Description of the Topographer

In the preferred embodiment, the cornea topographer consists of a light source to project a pattern light on the corneal surface, imaging optics to collect the light reflected by the cornea, a chiral optical mask and a photo-sensor converting light into a digital electronic signal. The chiral optical mask modulates the transmitted or reflected light such that the focusing error, originating from the mismatch between the object plane and the plane optically conjugate to the photo-sensor plane results in a displacement of the spatial spectrum of the registered image. The degree of displacement is evaluated by comparing the image spectrum with the reference spectrum represented, for example, by modulus of the OTF of the system in the absence of defocus. The focusing error, in turn, can be translated into the absolute distance to the corneal surface which information can be the basis for the corneal topogram.

Multiple defocus values or distance values can be obtained by dividing the corneal surface into multiple sub-regions and analyzing them individually. The defocus values represent the degrees of defocus, or distances, for chosen sub-regions of the cornea. Intensity distribution of the pattern light illuminating the cornea naturally defines the spacing, geometry and number of the sub-regions on the corneal image to be processed. For example, each sub-region can be a small rectangular area containing a single light spot when a grid of light spots is projected on the cornea.

Data processing form the corneal topographer includes a number of processing means for: (1)—transformation of the light image on the photo-sensor into a digital electronic signal and basic standard digital processing thereof, (2)—spectral decomposition of the sub-regions of the corneal image, (3)—evaluation of the degrees of displacement of the spatial spectra of the sub-regions of the corneal image relative to the reference images, conversion of said degrees of displacement into corresponding degrees of defocus, (4)—composition of a defocus-map, the intermediate for construction of a depth-map, and (5)—conversion of the degrees of defocus of the multiple sub-regions of the corneal image into in a depth-map.

Note that the imaging optics can be of any design including at least one refractive, or reflective optical element providing, in combination with the optical mask, close to diffraction-limited performance. The imaging optics can generally be designed such that it includes the, at least one, chiral optical mask as an integrated component.

Alternatively, the chiral optical mask can be integrated with the photo-sensor or implemented as a separate optical element. In the preferred embodiment a separate single prismatic refractive chiral mask is positioned in the exit pupil. This mask covers part of the aperture and a flat refractive element covers the remaining part. So, the optical mask includes, at least one, chiral optical element which comprises, at least one, prismatic surface covering only part of the mask aperture. The configuration of said prismatic surface can be further adjusted to optimize the optical function of the mask.

The optical mask modulates the light beam such that the spatial spectrum of the image changes position with change in defocus. Such change in position, displacement, can be a rotation, shift or scaling of the spatial spectra of the image, or a combination of said displacements. The dependency of the degree of said displacements on the degree of defocus should be known a priori, for example, from a theoretical analysis of the optical mask or from factory calibration. So, the degree of defocus can be estimated from the degree of displacement.

Digital processing means include,—basic imaging means such as transformation of the image by the photo-sensor into an digital electronic signal and additional standard electronic processing of images and, if required, final display means,—primary processing means, firstly, to perform spectral decomposition of the sub-regions of the corneal image, for example by Fourier transformation and, secondly, to provide degrees of displacement of the spatial spectra of the sub-regions of the corneal image relative to the reference spectrum,—secondary processing means, firstly, to convert said degrees of displacement into corresponding degrees of defocus of corresponding sub-regions of the cornea and, secondly, compose a defocus-map. The defocus-map is composed of defocus data from multiple selected sections, i.e. sub-regions, of the corneal image on the photo-sensor. Such defocus-map can be the final output, or is the intermediate step for constructing a depth-map by tertiary image processing means, which processing means, firstly, convert the degrees of defocus of the sub-regions of the corneal surface into distances, being absolute distances versus, for example, the first principal plane of the imaging optics, and, secondly, compose a depth-map containing relative distances between the sub-regions of the cornea.

The information on defocus and depth can be used to compose a corneal topogram, which topogram can be of various forms depending on the requirements. Note that the corneal topographer can provide various types of corneal topograms. Said defocus-maps and depth-maps are basic corneal topograms provided by the corneal topographer as set forth above. However, the topographer can also be expanded and adapted to provide, for example, a corneal topogram in the form of a wave-front map with aberration coefficients, preferably, as Zernike coefficients. Furthermore, with the necessary adaptations, a multispectral wave-front map can also be provided of the corneal surface which map compares corneal refraction versus wavelength. In this case, several wave-front maps, each obtained at a different wavelength, are combined into the multispectral wave-front map. Therefore, the term "corneal topogram" as used in the present document covers a variety of topograms as set forth above.

The topographer can also include additional units, for example, to represent the depth-map on a computer display, and additional means to, for example, transfer data directly to refractive surgical equipment or to, for example, contact lens manufacturing equipment.

The pattern light projected on the cornea must contain multiple high-contrast light features for the apparatus and method to work. For example, an equally-spaced grid of light spots can be projected on at least one surface of the cornea. In the preferred embodiment, a laser light source, in combination with a diffuser, or a pattern mask, and supporting optics provides a random speckle pattern, or a regular pattern, of light on the corneal surface. High-contrast features in the pattern light result in high-contrast features in the corneal image, which can be processed with the processing means and method as set forth in the present document. Dividing the corneal image into multiple sub-regions should provide at least one high-contrast feature for each sub-region of the corneal image.

Clearly, the laser light must be of a wavelength, for example, in the far-red or infra-red domain, and of an intensity as not to harm the eye, in particular the retina of the eye.

The topographer is adapted to, firstly, provide a defocus-map of the corneal surface, secondly, a depth-map of the corneal surface and, thirdly, a corneal topogram.

Note that construction of maps of other surfaces of the human eye, for example, surfaces of the crystalline lens, or even the surface of the retina, is not excluded. Clearly, the light source, the structure and the spectrum of the pattern light, and the imaging optics have to be adapted to provide a suitable image of the surface of interest. Also, digital processing steps have to be adapted, depending on the topographer arrangement, to maintain the accuracy of the measurements with increasing depth in the eye.

The method for cornea topography comprises—projection of a pattern light on, at least one, surface of the cornea,—collection of the light reflected by the corneal surface and projecting the reflected light onto a photo-sensor by imaging optics,—modulation of light by, at least one, optical mask such that the focusing error results in a displacement of the spatial spectrum of the corneal image relative to the reference spectrum,—basic processing means to transform an image on the photo-sensor into a digital electronic signal, additional standard digital image processing and, if required, image display,—primary processing to decompose the registered image into a spatial spectrum by spectral decomposition and to provide degrees of displacement of the spatial spectra of the sub-regions of the corneal image relative to the reference images,—secondary processing adapted to convert said degrees of displacement into multiple corresponding degrees of defocus of corresponding sub-regions of the cornea, and to compose a defocus-map and,—tertiary processing adapted to convert the multiple degrees of defocus of the sub-regions of the corneal surface into absolute distances, and to compose a depth-map containing relative distances between the sub-regions of the cornea.

In practice, the primary processing step can be performed, for example, by Fourier, or wavelet, decomposition of the sub-regions of the registered image followed by evaluation of the degrees of cross-correlation between the spectra of the image sub-regions and the reference spectrum (e.g. the modulus of the OTF) known a priory. In the second processing step, the degrees of cross-correlation can be recalculated into corresponding degrees of defocus, by using known a priory dependency of the, for example, the modulus of the OTF on defocus. Conversion of the degrees of defocus into absolute distances to the corneal sub-regions, performed by the tertiarly processing step, is a straightforward calculation which is described, for example, by Nayar et al. (Proc. of Fifth Intl. Conf. on Computer Vision, 995-1001, Cambridge, Mass., USA, 1995).

Mathematical Background and Mask Design

The described method for corneal topography requires, at least one, optical mask positioned inside or outside an imaging system, preferably in the plane of the exit pupil, to modulate the phase and the amplitude of the incoming light. The analysis below is directly applied to a single sub-image corresponding to a single sub-region of the cornea. The generalization to multiple sub-images is straightforward.

In Cartesian coordinates with the Z axis directed along the optical axis of the imaging system, and the X and Y axes perpendicular to the optical axis and lying in the plane of the exit pupil, the complex transmission of the mask can be expressed by $$P(x,y)=p(x,y)\exp[i\theta(x,y)], \tag{1}$$

where $p(x, y)$ is the amplitude transmission function and $\theta(x, y)$ is the phase function. For simplicity, the reduced coordinates (see, H. H. Hopkins, Proc. Roy. Soc. of London, A231, 91-103, 1955) are used in the formulas. Assuming that the focusing error caused by defocus amounts to $\phi$, the OTF as a function of the reduced spatial frequencies $\omega_x$ and $\omega_y$, $|\omega_x|$, $|\omega_y|\le 2$, becomes (see, H. H. Hopkins, Proc. Roy. Soc. of London, A231, 91-103, 1955)

$$H(\omega_x, \omega_y, \varphi) = \frac{1}{\Omega}\int_{-\infty}^{\infty}\int_{-\infty}^{\infty} P\left(x+\frac{\omega_x}{2}, y+\frac{\omega_y}{2}\right) \tag{2}$$
$$P^*\left(x-\frac{\omega_x}{2}, y-\frac{\omega_y}{2}\right)\exp[i2\varphi(\omega_x x+\omega_y y)]\,dx\,dy,$$

here $\Omega$ is the total area of the pupil in reduced coordinates $$\Omega = \int_{-\infty}^{\infty}\int_{-\infty}^{\infty} |P(x, y)|^2\,dx\,dy. \tag{3}$$

Specifying the spatial spectrum of the object as the Fourier transform of the object intensity distribution $$I_0(\omega_x, \omega_y) = \frac{1}{2\pi}\int_{-\infty}^{\infty}\int_{-\infty}^{\infty} I_0(x', y')\exp[-i(\omega_x x'+\omega_y y')]\,dx'\,dy', \tag{4}$$

where x' and y' are the transverse coordinates in the object plane and $I_0(x', y')$ is the intensity distribution that characterizes the object, the spectrum of the image (in the image plane) takes the form (J. W. Goodman, Introduction to Fourier Optics, McGraw-Hill Co., Inc., New York, 1996)

$$I_i(\omega_x,\omega_y)=H(\omega_x,\omega_y,\phi)I_0(\omega_x,\omega_y). \tag{5}$$

Thus, the spatial spectrum of the image is a product of the object spectrum and the OTF of the optical system with defocus. Note, that Eq. (5) is valid for isoplanatic imaging. The focusing error $\phi$ can be expressed, for example, as follows $$\varphi = \frac{\pi D^2}{4\lambda}\left(\frac{1}{f}-\frac{1}{z_o}-\frac{1}{z_i}\right), \tag{6}$$

where D is the diameter of the exit pupil; $\lambda$ is the wavelength; f is the back focal length; $z_o$ is the unknown a priori distance from the object to the first principal plain of the optical system; $z_i$ is the distance between the second principal plane and the image plane.

The complex function $P(x, y)$ has to be chosen such that the image spectrum $I_i(\omega_x,\omega_y)$, given by Eq. (5), converts defocus changes into detectable displacements of the spectrum features. The spectrum features, or a characteristic pattern of the spectrum, should be easily detectable and permit unambiguous quantitative determination of the focusing error $\phi$ from theses displacements. Among possible displacements of the spectrum features are lateral shift, rotation and scaling. Complex displacements including combinations of lateral shift, rotation and scaling are also admissible as soon as they allow quantitative determination of defocus irrespectively the spatial spectrum of the object $I_0(\omega_x, \omega_y)$.

For most combinations of $\theta(x,y)$ and $p(x,y)$, the analytical expression for $H(\omega_x,\omega_y,\phi)$, given by Eq. (2), can not be found explicitly. In the same time, numerical simulations can be carried out to predict spectrum displacement caused by defocus. Alternatively, a fully assembled optical system with the properly designed mask can be calibrated with an object positioned at different distances from the corneal topographer. With a discreet set of the experimentally registered degrees of displacements corresponding to a discreet set of distances an intermediate distance can be evaluated by, for example, interpolating the calibration data.

Quantitative determination of the focusing error $\phi$ requires comparison of the spatial spectrum of the image with the reference spectrum specified at any known a priori defocus. One of the simplest choices is to use the OTF of the optical system evaluated at $\phi=0$. In this case, the degree of displacement can be found by comparing $H(\omega_x,\omega_y,0)$ with $I_i(\omega_x,\omega_y)$. The magnitude of defocus, in turn, is evaluated by comparing $H(\omega_x,\omega_y,\phi)$ with $I_i(\omega_x,\omega_y)$, where $\phi$ is adjusted to get the closest match between $H(\omega_x,\omega_y,\phi)$ and $I_i(\omega_x,\omega_y)$. In many cases, but not always, the best match between $H(\omega_x,\omega_y,\phi)$ and $I_i(\omega_x,\omega_y)$ can be found by, for example, maximizing their cross-correlation function $$C(\phi)=\iint |H(\omega_x,\omega_y,\phi)|\times|I_i(\omega_x,\omega_y)|d\omega_x d\omega_y, \tag{7}$$

the maximum of $C(\phi)$ is reached when $\phi$ coincides with the unknown defocus. More complex comparison methods can be used, for example, based on moment analysis, circular harmonic correlation (see, J. W. Goodman, Introduction to Fourier Optics, McGraw-Hill Co., Inc., New York, 1996) etc.

Among the simplest implementations of the optical masks which, firstly, create distinct features in the image spectrum and, secondly, make position and size of the spectrum features dependent, in a certain way, on defocus is a rectangular aperture with a half-aperture prismatic element. The amplitude function of the mask is given by $$p(x, y) = \begin{cases} 1, & |x| \le 1 \text{ and } |y| \le 1 \\ 0, & \text{otherwise,} \end{cases} \tag{8}$$

and the phase function is specified as $$\vartheta(x, y) = \begin{cases} Ay, & x \ge 0 \\ 0, & x < 0. \end{cases} \tag{9}$$

It is clear that the phase function $\theta(x, y)$ according to Eq. (9) is a chiral function.

Assuming, for simplicity of calculations, that $|\omega_x|\le 1$ and $|\omega_y|\le 2$, the integration according to Eq. (2) with the mask specified by Eqs. (8-9) results in the OTF which can be represented as follows $$H(\omega_x,\omega_y,\phi)=\{a+2b\cos((\phi\omega_x+A\omega_y/2)\}\exp(iA\omega_y/2), \quad (10)$$

where the real coefficients a and b are $$a = \frac{\sin(\varphi\omega_x|\omega_x|)\sin([2-|\omega_y|][A/2+\varphi\omega_y])}{2\varphi\omega_x(A+2\varphi\omega_y)}, \quad (11)$$

$$b = \frac{\sin(\varphi\omega_x[1-|\omega_x|])\sin[\varphi\omega_y(2-|\omega_y|)]}{4\varphi^2\omega_x\omega_y}. \quad (12)$$

As follows from Eq. (10), the OTF contains a periodic structure, the said pattern of lines, which structure does not depend on the object structure at all, but is sensitive to defocus. Note that at $\phi \to 0$ and $A \to 0$, the OTF simplifies to $$H(\omega_x,\omega_y,\phi=0)=(1-|\omega_x|/2)(1-|\omega_y|/2), \quad (13)$$

which is the OTF of a diffraction-limited system with a square pupil.

The phase in Eq. (17) is represented by a linear function of spatial frequencies $\omega_x$ and $\omega_y$, $$\Phi=\phi\omega_x+A\omega_y/2. \quad (14)$$

Introducing notations $$\begin{cases} \omega_x = \omega\cos\alpha, \\ \omega_y = \omega\sin\alpha, \end{cases} \text{ and } \begin{cases} \omega = \sqrt{\omega_x^2+\omega_y^2}, \\ \alpha = \arctan(\omega_y/\omega_x), \end{cases} \quad (15)$$

Eq. (14) can be rewritten $$\Phi=\omega\sqrt{\phi^2+A^2/4}\cos(\alpha-\beta), \quad (16)$$

where $\beta=\arctan[A/(2\phi)]$ is the angle perpendicular to the line pattern.

From Eq. (16), it follows that the line pattern is rotated by the angle $\alpha=-\pi/2+\beta$ about the origin ($\alpha<0$ when $A>0$ and $\phi>0$). At $\alpha=\beta$ the spatial period T of the line pattern structure reaches its minimum $$T=2\pi/\sqrt{\phi^2+A^2/4}. \quad (17)$$

So, the pattern orientation specified by the angle $$\alpha=-\pi/2+\arctan[A/(2\phi)] \quad (18)$$

and its spatial period, given by Eq. (17), vary, in a known manner, with the focusing error $\phi$.

DETAILED DESCRIPTION OF THE PREFERRED EMBODIMENT

Figure 1:
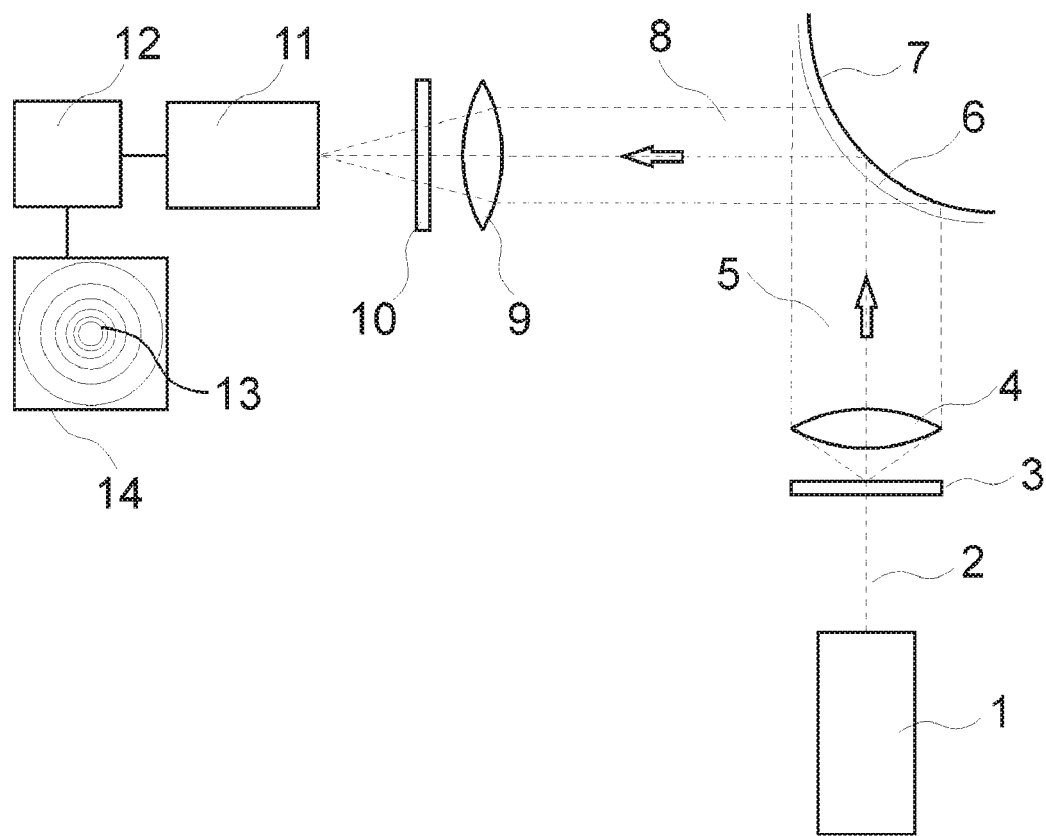
FIG. 1 is a cornea topographer according to the invention.

FIG. 1. Cornea topographer design. A light source, 1, produces a light beam, 2, illuminating a patterned mask, 3. An objective, 4, projects the light, 5, on the eye to create pattern light, 6, on the cornea, 7. Reflected light, 8, is collected by an objective, 9, and imaged through an optical mask, 10, onto a photo-sensor, 11. Modulation of light by the optical mask, 10, results in characteristic features in the spatial spectrum of the registered image. The degree of displacement of these features with respect to the reference spectrum is evaluated by the processing means, 12, for a number of sub-images of the registered image. The processing means, 12, calculate also the degrees of defocus and absolute distances from each sub-region of the corneal surface, corresponding to the processed sub-images, to the objective, 9, or any other well-defined plane. The resulting data are depicted as a depth map, 13, representing the sampled three-dimensional surface of the cornea on a display, 14, representing the corneal topogram.

Figure 2:
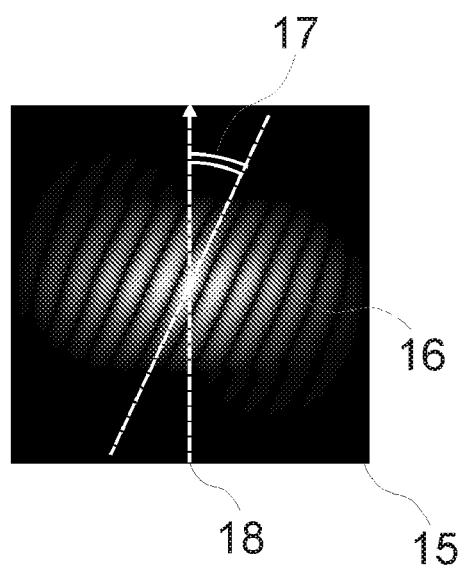
FIG. 2 is an example of a spatial spectrum of a conical image.

FIG. 2. Example of the spatial spectrum of a corneal image. Spatial (power) spectrum, 15, of the corneal image is composed, in this example, of parallel lines, 16, that rotate by an angle, 17, with respect to the reference position, 18, corresponding to zero defocus. The degree of rotation, 17, uniquely indicates the degree of defocus in the registered image.

The invention claimed is:

1. A cornea topographer comprising:
   at least one light source to project a pattern light on at least one corneal surface,
   imaging optics to collect light reflected by the at least one corneal surface, and project a corneal image onto a photo-sensor,
   at least one optical mask to modulate the light reflected by the at least one corneal surface such that the degree of defocus of the corneal image on the photo-sensor relative to an in-focus plane results in displacements of an image spatial spectrum relative to a reference spectrum, and
   at least one processor configured to:
      transform an image on the photo-sensor into a digital electronic signal,
      perform spectral decomposition of a plurality of sub-regions of the corneal image, and measure the degrees of displacement of the spatial spectra of each of the plurality of sub-regions of the corneal image relative to the reference spectrum,
      convert said degrees of displacement into corresponding degrees of defocus of multiple corresponding sub-regions of the cornea, and
      convert said multiple degrees of defocus into absolute distances.

2. The cornea topographer according to claim 1, wherein the at least one processor is further configured to combine the degrees of defocus of multiple corresponding sub-regions of the cornea into a defocus-map of the cornea.

3. The cornea topographer according to claim 1, wherein the at least one processor is further configured to combine the relative distances between the multiple sub-regions of the cornea into a depth-map of the cornea.

4. The cornea topographer according to claim 2, wherein the at least one processor is further configured to combine the information on defocus and depth to provide a corneal topogram; and
   cause said corneal topogram to be displayed on an image display.

5. The cornea topographer according to claim 1, wherein the light source comprises a laser adapted to project a pattern light on at least one corneal surface.

6. A method for cornea topography comprising:
   projecting a pattern light on at least one corneal surface,
   collecting light reflected by the at least one corneal surface and projecting a corneal image onto a photo-sensor using imaging optics,
   modulating the light reflected by the corneal surface using at least one optical mask such that a focusing error results, causing a displacement of the spatial spectrum of the corneal image relative to a reference spectrum, and using at least one processor:
  transforming the corneal image into a digital electronic signal,
  decomposing a registered image of each of a plurality of sub-regions of the corneal image into a spatial spectrum to determine the degrees of displacement of the spatial spectrum of each sub-region relative to a reference image,
  converting said degrees of displacement into degrees of defocus for each of the plurality of sub-regions,
  composing a defocus map based at least partially on the degrees of defocus for each of the plurality of sub-regions,
  converting the multiple degrees of defocus of the sub-regions into absolute distances, and
  generating a depth-map comprising relative distances between the sub-regions of the cornea.

\* \* \* \* \*